US010750999B2

(12) United States Patent
Parks et al.

(10) Patent No.: US 10,750,999 B2
(45) Date of Patent: Aug. 25, 2020

(54) EXTENDED BALLOON ASSEMBLY FOR A CATHETER

(71) Applicant: Covidien LP, Mansfield, MA (US)

(72) Inventors: Thomas R. Parks, Mammoth Lakes, CA (US); Sorin Marius Gorgan, Redondo Beach, CA (US)

(73) Assignee: COVIDIEN LP, Mansfield, MA (US)

( * ) Notice: Subject to any disclaimer, the term of this patent is extended or adjusted under 35 U.S.C. 154(b) by 492 days.

(21) Appl. No.: 15/319,929

(22) PCT Filed: Jun. 19, 2015

(86) PCT No.: PCT/US2015/036545
§ 371 (c)(1),
(2) Date: Dec. 19, 2016

(87) PCT Pub. No.: WO2015/195991
PCT Pub. Date: Dec. 23, 2015

(65) Prior Publication Data

US 2017/0128012 A1 May 11, 2017

Related U.S. Application Data

(60) Provisional application No. 62/014,773, filed on Jun. 20, 2014.

(51) Int. Cl.
*A61B 5/00* (2006.01)
*A61B 5/03* (2006.01)
(Continued)

(52) U.S. Cl.
CPC ............ *A61B 5/6853* (2013.01); *A61B 5/036* (2013.01); *A61B 5/1073* (2013.01);
(Continued)

(58) Field of Classification Search
CPC ..... A61B 5/036; A61B 5/1076; A61B 5/6853; A61M 25/00; A61M 25/0021–0023;
(Continued)

(56) References Cited

U.S. PATENT DOCUMENTS 5,058,603 A * 10/1991 Doi ........................ A61B 1/018
600/587
7,967,835 B2 6/2011 Rehnke
(Continued)

FOREIGN PATENT DOCUMENTS

CN 1418709 5/2003
CN 102791180 11/2012
(Continued)

OTHER PUBLICATIONS

Office Action from corresponding Chinese Appl. No. 2015800399673 dated Aug. 5, 2019.

*Primary Examiner* — Daniel L Cerioni
*Assistant Examiner* — Raymond P Dulman
(74) *Attorney, Agent, or Firm* — Pearl Cohen Zedek Latzer Baratz LLP

(57) ABSTRACT

A balloon assembly for an anorectal manometry catheter may include a three-part tube and a balloon mountable on the tube. The three-part tube may include a flexible proximal connection tube (PCT), a flexible distal connection tube (DCT), and a semi-flexible transfer tube that is interposed between and connected to each of said PCT and said DCT. The balloon may have a first opening connected to a first end of the transfer tube and a second opening connected to a second end of the transfer tube which is opposite the first end of the transfer tube. The three-part tube may be configured to be slidable along and over a catheter in a first direction, with the DCT slid first. The three-part tube may also be configured to be slidable over the catheter in the opposite
(Continued)

direction such that the PCT is folded onto itself and completely contained in the transfer tube.

11 Claims, 9 Drawing Sheets

(51) Int. Cl.
*A61B 5/22* (2006.01)
*A61B 5/107* (2006.01)

(52) U.S. Cl.
CPC ............ *A61B 5/1076* (2013.01); *A61B 5/227* (2013.01); *A61B 5/4255* (2013.01); *A61B 5/6885* (2013.01); *A61B 2562/0247* (2013.01)

(58) Field of Classification Search
CPC .. A61M 25/0026–0029; A61M 25/003; A61M 25/10; A61M 25/1025; A61M 2025/0024–0025; A61M 2025/0039–004
See application file for complete search history.

(56) References Cited

U.S. PATENT DOCUMENTS

| | | | | |
|---|---|---|---|---|
| 2004/0215140 | A1 | 10/2004 | Forman | |
| 2007/0250101 | A1 | 10/2007 | Horn et al. | |
| 2010/0113939 | A1 | 5/2010 | Mashimo et al. | |
| 2012/0148175 | A1 | 6/2012 | Wesselmann | |
| 2013/0023920 | A1 | 1/2013 | Terliuc et al. | |
| 2014/0046411 | A1* | 2/2014 | Elkins | A61F 7/00 607/104 |
| 2014/0336569 | A1 | 11/2014 | Gobel | |
| 2015/0216580 | A1* | 8/2015 | Mihalik | A61B 18/02 606/21 |
| 2015/0313473 | A1* | 11/2015 | O'Neill | G01K 11/3206 600/414 |

FOREIGN PATENT DOCUMENTS

| | | |
|---|---|---|
| DE | 10 2012 008663 | 2/2013 |
| WO | WO 2012/164559 A1 | 12/2012 |

* cited by examiner 410
442
470
460
V2
482
460
V1
430
S1
412
416
S11
S12
450
450A
450B
414
440
S2
480
490
492
494
496
450B,460

EXTENDED BALLOON ASSEMBLY FOR A CATHETER

CROSS-REFERENCE TO RELATED APPLICATIONS

This application is a National Phase Application of PCT International Application No. PCT/US15/36545, International Filing Date filed Jun. 19, 2015, claiming priority from U.S. Provisional Patent Application No. 62/014,773, filed Jun. 20, 2014, all of which are hereby incorporated by reference.

FIELD OF THE INVENTION

The present invention generally relates to catheters and more specifically to an assembly for extending the positional sensing range, and generally enhancing the sensing capability, of an anorectal manometry catheter.

BACKGROUND

The term, or physiological property called, "rectal capacity" refers to the volume of the rectum. This physiological property is measured approximately—for example by using a high compliance balloon of suitable geometry—by looking at the amount of air or liquid used to fill the balloon up to the point where the pressure that is required to further inflate the balloon rises appreciably above a baseline (e.g. near intra-abdominal pressure). The term, or physiological property called, "rectal compliance" is a measure of the distention elasticity of the rectum. It is taken as the measured change in pressure inside the balloon divided by the change in balloon fill volume (air or water), typically after the balloon has filled the un-stretched (un-distended) organ.

Rectal compliance and rectal capacity have significant bearing on lower gastrointestinal (GI) function and dysfunction (e.g., diarrhea and constipation). Rectal compliance and rectal capacity measurements are currently done as separate tests from the more commonly employed anorectal manometry studies that are based on physiological pressure that is measured/sensed in the anal canal and rectal cavity. For example, reduction in the compliance of the rectum, which shortens the time between sensation of stool and the urgent need to have a bowel movement, may cause or result in fecal incontinence. Surgery or radiation injury can scar and stiffen the rectum. Inflammatory bowel disease can also make the rectum less compliant. Currently, anorectal manometry catheters that are designed for anal and rectal evaluation use a short balloon that does not enable evaluation of the rectal capacity and rectal compliance.

SUMMARY

While using a conventional anorectal manometry catheter is beneficial in measuring pressure in the anal canal and anal sphincter, it would be beneficial to have an extended balloon assembly that, after assembling on a conventional anorectal manometry catheter, would enhance the pressure measurement capability of the catheter to the extent that the rectal capacitance and rectal compliance could be measurable as well.

The terms 'proximal' and 'distal', as used herein, refer to an object (e.g., a catheter, a tube, a section of a tube) and to an end or side of an object (e.g., an end of a catheter, tube, tube section and balloon, etc.) that, during insertion of the object (e.g. a catheter with a balloon assembly) into the rectum, respectively enter the anus first and last. For example, a proximal end of an object (e.g., tube, tube section) enters the anus before the distal end of that object, and a proximal connection tube or section of a multi-sectional tube (e.g., two-section tube, three-section tube) enters the anus before a distal connection tube or section of the multi-sectional (e.g., three-section tube).

A retrofitted anorectal manometry catheter may include an anorectal catheter (AR) and a retrofitting balloon assembly that is mountable on the catheter. The catheter may include a number N of pressure sensors (N=1, 2, . . . , n; e.g., N=13), where a number N1 (N1<N) of sensors (e.g., N1=10) may be used to measure pressure caused, for example, by at least the anal sphincter, and a number N2 (N2=N−N1) of sensors (e.g., N2=2) that may be used to measure pressure caused by more internal organs such as aspects of the rectum in conjunction with general abdominal pressure.

The balloon assembly for the anorectal manometry catheter may include a balloon and a flexible assembly tube (e.g., three-section tube) that is mountable on the catheter to facilitate, or enable, mounting of the balloon on the catheter. The flexible assembly tube mountable on the catheter may be implemented as one assembly tube that may include three distinct tubular sections (that may have different or alternating rigidness), or as two tubes that may be connected lengthwise and may similarly include the three tubular sections or similar tubular sections, or as three tubes that may be connected lengthwise and similarly include or embody the three tubular sections, hence the terms "three-part tube" and "three-section tube", which may be used interchangeably. The three-section tube may be configured to encircle at least a portion of a catheter and it may be concentrically slidable along and over the catheter in a first direction. The three-section tube may include a flexible proximal connection tube or section ("PCT"), a flexible distal connection tube or section ("DCT"), and a semi-flexible (less flexible than the PCT and DCT) transfer tube or section that is lengthwise interposed between, and connected to each of the PCT and the DCT. The balloon, which may be mounted on the three-section tube, may have a first opening which is, or may be, connected in an airtight fashion to a first end of the transfer tube/section, and a second, e.g., opposite, opening which is, or may be, connected in an airtight fashion to a second/opposite end of the transfer tube/section.

The PCT may be concentrically foldable, at least partly, inside or into the transfer tube/section to enable concentric sliding of the transfer tube/section and DCT along and over the catheter in a backwards direction (e.g., in a second direction which is opposite the first direction). The balloon may be inflated through the transfer tube/section. For example, the transfer tube/section may include a through hole or air passage to enable inflation of the balloon.

The transfer tube/section may include a bulge to protect a pressure sensor included in the catheter from external or extraneous pressure, which may be a pressure other than a pressure inside the balloon (e.g. contact pressure that might arise from contact of the transfer tube/section with the sensor). The bulge may be stiffened. The bulge may include a through hole or air passage to enable measurement of pressure inside the balloon by pressure sensors included in the catheter. The bulge may include a through hole or air passage to enable inflation of the balloon. The same through hole or air passage may be used for both inflating the balloon and measuring pressure inside the balloon, or balloon inflation and pressure measurement may be performed using separate through holes or air passages. (The transfer tube/section may not include a bulge.)

The 'free' diameters of the PCT, transfer tube/section and DCT may respectively be within the 8.5 mm-10 mm (but may be 4 mm-10 mm), 8 mm-9.5 mm (but may be 4 mm-10 mm) and 5.5 mm-6.5 mm (but may be 4 mm-10 mm) ranges, though a diameter of any of the tubes or tubular sections may exceed or differ from the respective range. These sizes may vary or be different to suit the size of the catheter actually used. For example, a standard catheter diameter used by some AR catheter manufacturers for AR testing is 9 mm, and certain multi-dimensional pressure imaging AR catheters may have a diameter of approximately 11 mm. Of course, the balloon assemblies and the balloon assembling methods described herein are not limited to any particular catheter length, diameter or thickness, as they may be adapted or suited to the catheter used. By 'free diameter' of a connection tube is meant a diameter of the connection tube in a 'relaxed' state or 'normal' state, which is the state of the connection tube, or part thereof, before it is stretched to a larger diameter in order to enable it to be bonded or attached to the transfer tube. Catheters, and therefore connection tubes/sections and transfer tube/sections, having smaller or larger diameters and/or different thicknesses than described herein may be used.

The wall thicknesses of the PCT, transfer tube/section and DCT may respectively be within the 0.01 mm-0.5 mm, 0.1 mm-4 mm and 0.01 mm-0.5 mm ranges, though a thickness of any of the tubes or sections, or segments of such tubes or sections may exceed, or differ from, the respective range. The PCT may be made of a soft, supple and biocompatible material (e.g., plastic) such as TSP-1051 polyurethane (or TSP-1066 polyurethane; e.g., 2.2 mil thick), which is produced by Polyzen Inc., or another polyurethane or a polyurethane based/including material, or, for example, a suitable thermoplastic elastomer ("TPE"). The DCT may be made of TPE (e.g., XFlex SEBS; 'SEBS'—Styrene-Ethylene-Butylene-Styrene). The transfer tube/section may be made of Polyurethane (Tubing) material, which is a semi-rigid material. (The transfer tube/section may be less flexible than the proximal tube/section and the distal tube/section.) Of course, the transfer tube and the connection tubes may be produced from other or different materials than the ones mentioned herein.

An embodiment of a method for mounting the balloon assembly on the anorectal manometry catheter may include concentrically sliding the three-section flexible tube along and over the catheter, in a first direction, until a proximal end of the PCT lines up, or is aligned, with a proximal attach point on the catheter, then securing in an air-tight or nearly air-tight fashion the proximal end of the PCT to the proximal attach point on the catheter; then sliding the transfer tube/section and the DCT backwards; e.g., in a second direction opposite the first direction, over the catheter and towards the proximal end of the catheter, until a distal end of the DCT lines up, or is aligned, with a distal attach point on the catheter, then securing in an air-tight or nearly air-tight fashion the distal end of the DCT to the distal catheter attach point. Securing the proximal end of the PCT to the proximal catheter's attach point and securing the distal end of the DCT to the distal catheter's attach point may be implemented by a rubber band or by a string type material such as suture or dental floss. The balloon may be attached to the transfer tube or transfer section either before or after the three-section tube is slid over and along the catheter. The balloon may be attached to the PCT and DCT at or near where they connect to the transfer tube. The balloon may be attached at two locations or only at one location on the transfer tube or transfer section before-hand. In other embodiments the assembly tube may include a transfer tube and a DCT, but not a PCT.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

The description that follows provides various details of exemplary embodiments. However, this description is not intended to limit the scope of the claims but instead to explain various principles of the invention and the manner of practicing it.

Unless explicitly stated, the embodiments of methods described herein are not constrained to a particular order or sequence of steps, operations or procedures. Additionally, some of the described method embodiments or elements thereof can occur or be performed at the same point in time.

Figure 1:
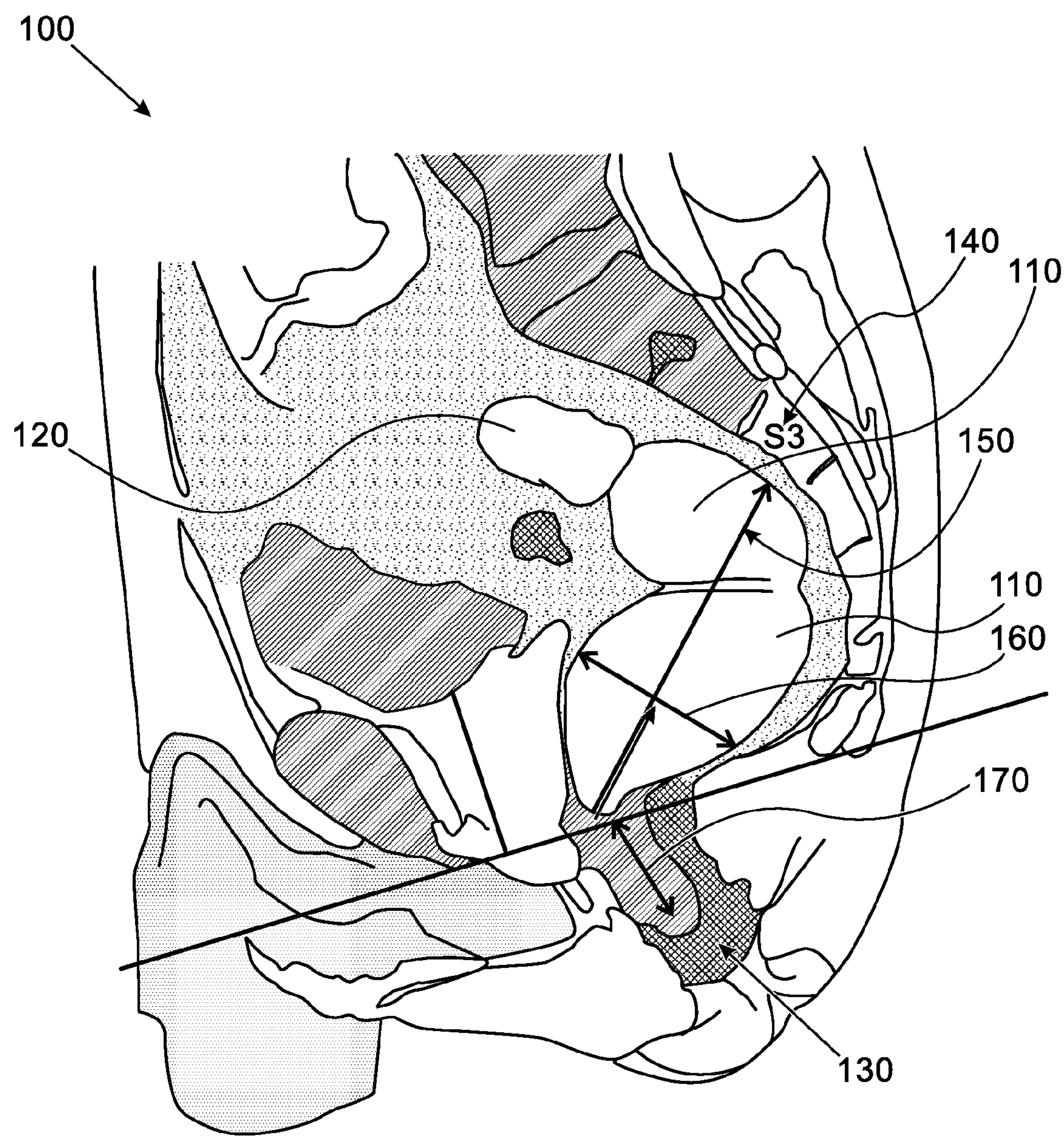
FIG. 1 is schematic cross-section of the lower part of the digestive system (prior art)

FIG. 1 shows an illustration representing an MRI image 100 showing, among other things, a rectum filled with 250 milliliter ultrasound-grade gel (the 'ultrasonic' gel is represented by white areas 110 and 120 in FIG. 1) labeled with the radiographic contrast material Gadolinium. (During the imaging process the patient was lying in semi-supine position within the MRI scanner). The rectum is shown in FIG. 1 filled with gel (110), and some of the gel (shown at 120) entered the sigmoid part/section. (Gel areas 110 and 120 show that the reservoir available for accommodating stool is larger than the rectum alone).

The length (of sagittal section 150) of the rectum from the anus (130) to a fixed landmark (e.g., s3 vertebra, shown at 140) is, on the average, 10 centimeters (with minimum 7 cm and maximum 14 cm) measured over 20 patients. The diameter (160) at this volume distension located 5 cm from proximal anal verge) is about 6 cm. The rectum is roughly cylindrical and its diameter changes depending on the distance between the anal verge and the respective position in the rectum.

The rectum capacitance and rectum compliance can be measured by using an elongated balloon that is long enough to occupy the length/space between anal sphincter 170, or a few centimeters behind it, and the distal end of the sigmoid colon (pelvic colon), which is near the spinal bone referred to as 's3 vertebra', and large enough in diameter (160) to cover most, if not all, of the rectal volume mentioned above.

Figure 2:
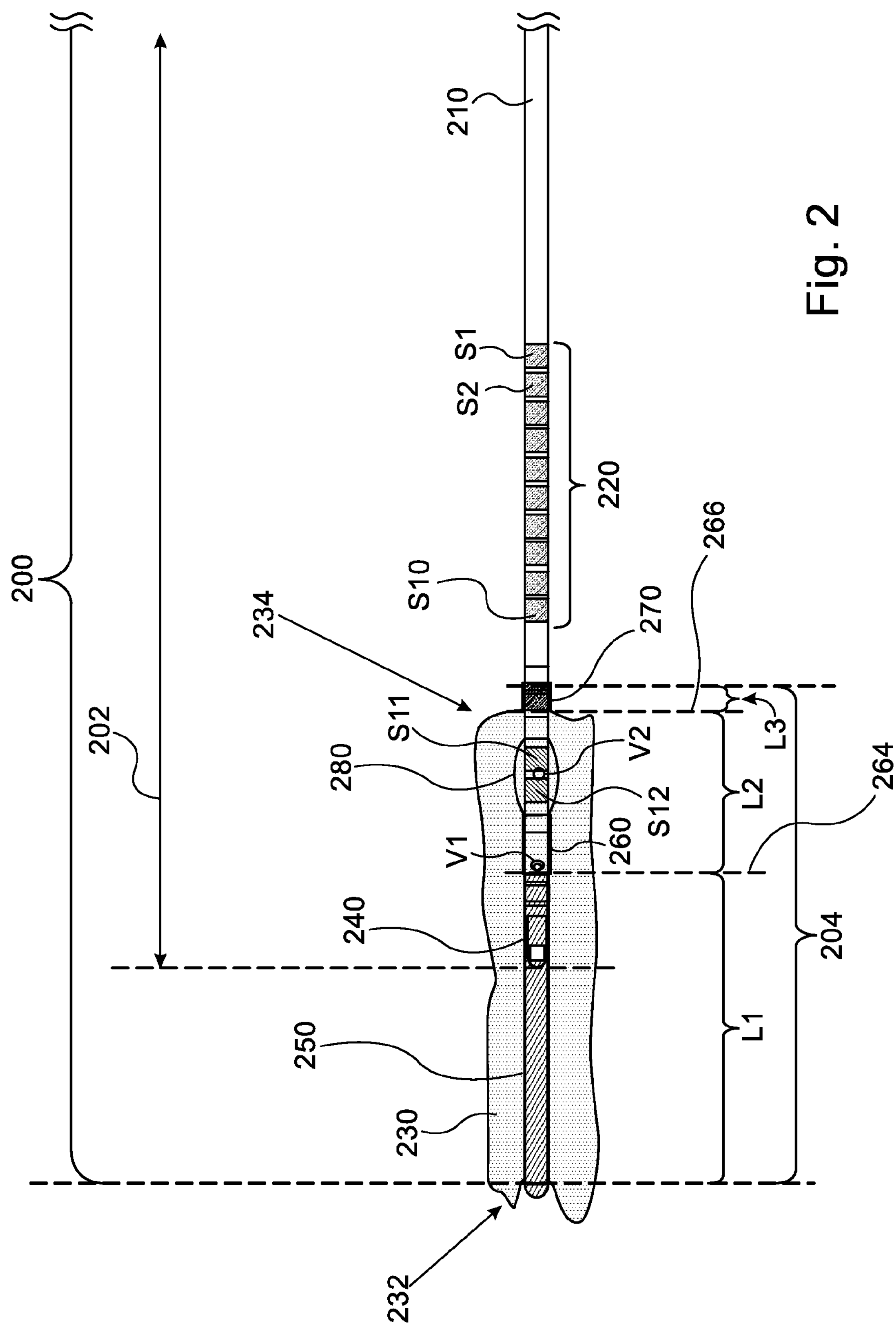
FIG. 2 shows a (retrofitted) anorectal manometry catheter according to an example embodiment of the invention.

FIG. 2 shows an anorectal manometry catheter assembly 200 according to an example embodiment of the present invention. Anorectal manometry catheter assembly 200 may include a manometry catheter 210 having an overall length 202, and an add-on balloon assembly 204. Balloon assembly 204 may include a three-part tube and a balloon, as described herein.

Catheter 210 may include one or more (e.g., an array of) sensing elements, or sensors, for measuring one or more types of physiological parameters. For example, catheter 210 may include twelve pressure sensors, ten of which are shown at 220 (these sensors are designated as sensors S1, S2, S3, . . . , S10) and another two sensors are designated as S11 and S12. Sensors S1-S10 are typically used to measure pressure in (caused by) the anal sphincter. Sensors S11-S12 may be used in conjunction with a relatively short balloon, via which sensors S11-S12 may sense pressure, to measure pressure in the rectum. However, a catheter using a short balloon has a drawback: a short balloon cannot fully fill the rectum and, therefore, cannot provide pressure measurements suitable for evaluation of rectal capacity and rectal compliance.

Referring to FIG. 2, an elongated balloon 230 is mounted on catheter 210 using an embodiment of the assembly method described herein. Balloon 230 may be attached to, or mounted on, catheter 210 by using a three-section flexible tube that may include lengthwise connected flexible tubes (e.g., three tubes) or tube sections (e.g., three tubular sections) whose material(s) and flexibility are selected such that they enable elongated balloon 230 to be fully and conveniently inserted through, and snugly fit into, the entire most of, or the majority of, the length of the rectum and completely occupy the volume of most, if not all, parts/sections of the rectum. The tubes or tubular sections forming the tube may be concatenated such that a 'semi-flexible' or somewhat flexible tube/section, which is referred to herein as "transfer tube" and "transfer section", is interposed between two, more flexible, tubes or tubular sections which are referred to herein as "connection tubes" or "connection sections". To distinguish between the two connection tubes or tubular sections, one connection tube/section is referred to herein as "proximal connection tube" (PCT) or "proximal connection section", and the other connection tube/section is referred to herein as "distal connection tube" (DCT) or "distal connection section". As defined above, the term 'proximal' refers to an object (or to an object's end) that, during insertion of the catheter into the rectum, enters the anus before another object (or another object's end) does. The other object (or other object's end) is referred to herein as 'distal'.

Referring again to FIG. 2, the proximal end of catheter 210 is shown at 240. Balloon 230 has a proximal end/opening 232 and a distal end/opening 234. A first flexible tube or section 250 (a PCT) having a length L1 may lengthwise and contiguously be connected (by its distal end) to, or be an extension of, a proximal end 264 of a second tube or section 260 (a transfer tube/section) that may have a length L1+L2. (The PCT may have a length L1 inside the transfer tube/section.) (The PCT and transfer tube are connected at the left side of L1.)

The other (e.g., opposite or distal) end 266 of transfer tube/section 260 may lengthwise and contiguously be connected (by its distal end) to, or be an extension of, a proximal end of a third tube/section 270 (a DCT) having length L3. Transfer tube/section 260 is lengthwise interposed between PCT 250 and DCT 270, to form therewith one, continuous, tube. Balloon proximal end/opening 232 and distal end/opening 234 may be connected or attached to transfer tube/section 260.

PCT 250 and DCT 270 may be made of flexible material (s), and transfer tube/section 260 may be made of 'semi-flexible' material(s), that is, transfer tube/section 260 may be made of a material(s) that is/are less flexible than the material(s) of PCT 250 and DCT 270. For example, transfer tube/section 260 may be made of or include polyurethane (e.g., C-210-A polyurethane), and PCT 250 and DCT 270 may be made of or include a more flexible material, for example Polyurethane (e.g., TSP-1051 polyurethane) or a material including polyurethane. In some embodiments, tubes/sections 250, 260 and 270 may be made of or include other materials or additional materials, provided that each tube/section has the physical properties designated or desired for that tube/section. (The PCT should be flexible enough to enable turning it inside out; e.g., folding it concentrically 'on itself'. The DCT can be as flexible as the PCT or somewhat less flexible, and the transfer tube/section should be semi-flexible; that is, in one embodiment it can to be flexible enough to enable easy insertion thereof into the rectum, and, yet, it should be rigid enough to mechanically sustain or support the entire balloon assembly/structure, for example, in order to prevent the balloon from collapsing, buckling or entangling when the balloon is inserted and then inflated in the rectum to its full design inflation volume, or from buckling during insertion into the rectum.)

The balloon assembly, which may include balloon 230, PCT 250 and DCT 270 and transfer tube/section 260, may be assembled onto catheter 210 such that a portion of transfer tube/section 260 circumferentially encompasses pressure sensors S11 and S12. Transfer tube/section 260 may have or include, at the portion encompassing sensors S11-S12, a bulge such as bulge 280. Sensors S11-S12 may be located on catheter 210 relative to the balloon assembly 204 such that the sensors can uninterruptedly sense the pressure inside balloon 230. Bulge 280 may be stiffened or reinforced in order to mechanically protect sensors S11-S12 from unwanted (e.g., extraneous) pressure that may be detrimental to the proper operation of these sensors during performance of anorectal procedures. (An extraneous pressure may be, for example, any pressure other than the pressure inside balloon 230.)

Transfer tube/section 260 may have one or more vent/through holes, (e.g., two vent/through holes, designated as V1 and V2) or air passages. (Two holes, if positioned correctly, for example as shown in FIG. 2, can prevent obstruction of air path when catheter 210 is flexed.) On the one hand, the vent/through holes (e.g., vent/through holes V1 and V2) or air passages enable inflation of balloon 230 (e.g., by using a conventional inflation system that is used with conventional catheters), and, on the other hand, the vent/through holes or air passages enable pressure sensors S11-S12 to measure the pressure, or pressure changes, inside balloon 230.

Balloon 230 may be made of, or include, a thin flexible material (e.g., TSP-1051 polyurethane with 1.5 mil thickness (±0.4 mil). (TSP-1051 polyurethane can be used in layers that are 1 mil to 2 mil thick.) (The flexible material of the balloon may be within the 1-2 mil, but other thickness ranges may be used, for example, 0.5-4 mil, or a thickness that is greater than 4 mil or less than 0.5 mil.) Using TSP-1051 (or a similar material), balloon 230 can inflate inside the rectum such that it occupies most, if not all, of the space within, or defined by, the rectum. The material and size of balloon 230 may be selected such that it enables the balloon to inflate to its maximum design volume that may be derived from the actual rectal volume/space to be filled up, which may be patient physiology specific. (The material and size of balloon 230 may accommodate for a range of possible patient physiologies.) In some embodiments, the balloon serves as an 'air bag', so it does not need to be made of a very stretchy elastic material; it needs to be flexible enough to be fully inflated, and it needs to be able to hold air up to a moderate pressure. This can be accomplished using a variety of thin flexible plastic materials.

On the average, the rectal volume is approximately 250 cubic centimeter ("cc"), and in some embodiments the balloon may be designed to accommodate some additional volume margin. For example, the balloon may be designed such that its maximum inflation volume is, say, 500 cc, though other designs may include other maximum inflation volumes, for example up to 400 cc, or up to 750 cc. (The balloon may be subjected to an external physiological pressure during use, e.g. pressure exerted on the balloon's outer surface by body organs (e.g., rectum.) Balloon 230 differs from balloons which are used in conventional anorectal manometry procedures in that balloon 230 is significantly longer than conventional balloons. (The transfer tube may be designed to extend through most or all of the rectum to enable the desired capacity and compliance measurements, and balloon 230 may be approximately 2-3 times longer than conventional balloons, and its diameter, when fully inflated, may be about 1.5 times or more/greater than the diameter of conventional balloons.)

Balloon 230 may be secured in place on catheter 210 using for example rubber bands. (Example rubber bands are shown, for example, in FIG. 4A (rubber band 414) and in FIG. 4D (rubber band 480).) The balloon may preferably be permanently bonded to the transfer tube, so that all a user needs to do is connect them to the catheter (e.g., per FIGS. 3 and 4). The PCT and DCT may be connected to the catheter using dental floss or rubber band.

Balloon 230 may be constructed, for example, of two disk-like sheets of plastic that may be welded, for example to a cylindrical central tube, to form therewith a tube-shaped or capsule-shaped balloon. The balloon may be manufactured using other techniques. For example, a simple way to manufacture a balloon would be to take a tubular shape and pinch/bunch together the ends at the attach points. (The tube shaped balloon may assume the shape of a capsule when it is inflated.)

Pushing an elongated balloon through the anus and into the rectum requires an 'element' that can lead the balloon through the anus and into the rectum. Therefore, a balloon that would 'simply' be attached to the tip of a catheter would not be a good solution. The tube disclosed herein enables easy insertion of an elongated balloon through the anus and into the rectum, as the semi-flexible transfer tube/section is, on the one hand, flexible enough to enable convenient insertion of the balloon assembly, and, on the other hand, stiff enough to lead the balloon through the anus and properly extend through the rectum. The balloon in one embodiment should extend more proximally into the rectum (effected via the proximally extending transfer tube/section) than would be achievable by simply attaching the balloon to the end of a typical AR catheter. The transfer tube/section also constrains the balloon (by controlling its proximal and distal ends) to keep it properly positioned in the rectum when the main sensor array of the catheter is positioned in the anal canal. A benefit of this positioning of the balloon is that it is kept away from the main sensor array in the anal canal during diagnostic measurements and thereby does not interfere with these measurements. The balloon assembly is an extension of the AR catheter, and the way the balloon assembly is designed/structured and mounted on the AR catheter enables dedicated pressure sensors on the AR catheter (e.g., sensors S11 and S12) to 'remotely' sense rectal compliance and rectal capacity without interfering with the other function of the AR catheter, which is sensing pressure in the anal canal by, for example, sensors S1-S10.

Figure 3:
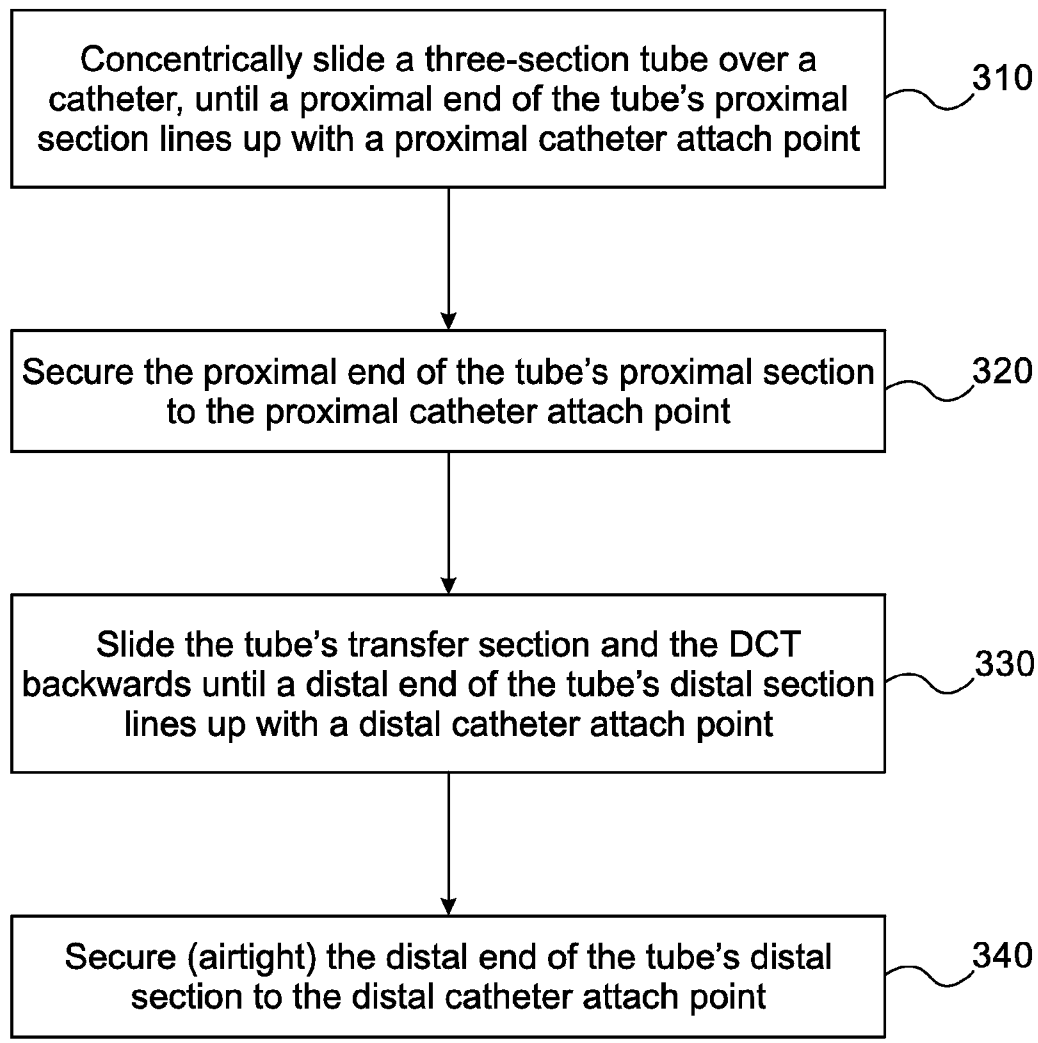
FIG. 3 shows a method for mounting a balloon assembly on an anorectal manometry catheter according to an example embodiment of the invention.

FIG. 3 shows a method for mounting a balloon assembly on a catheter according to an example embodiment of the present invention. FIG. 3 will be described in association with FIGS. 4A-4D, which pictorially show respective assembly steps. At step 310, a tube having a central section (e.g., transfer tube/section 460) interposed between two connection sections; e.g., a three-section tube including a PCT 450, a transfer tube/section 460 (optionally with a protective bulge 482) and a DCT 470 (one connection section), may concentrically be slid along and over catheter 410 in a first direction (e.g., in direction 412), for example from proximal end 440 of catheter 410 to distal end 442 of catheter 410. (DCT 470 may be slid over the catheter first, then may follow the transfer, or central, tube/section 460, and, finally, PCT 450.) Balloon 430 may be attached (in airtight manner) to transfer tube/section 460, for example by using glue (e.g., epoxy), either before or after the three-section tube is slid over catheter 410. Balloon 430 may be attached to transfer tube/section 460 by connecting a first opening of the balloon to a first end of the transfer tube/section and connecting a second opening of the balloon to a second end of the transfer tube/section. A single balloon attachment may be used, where a first opening of the balloon is connected to an end of the transfer tube/section and a second opening of the balloon is non-existent or sealed/bond, as shown, for example, in FIGS. 6A-6B.

Figures 4A, 4B, 4C, 4D:
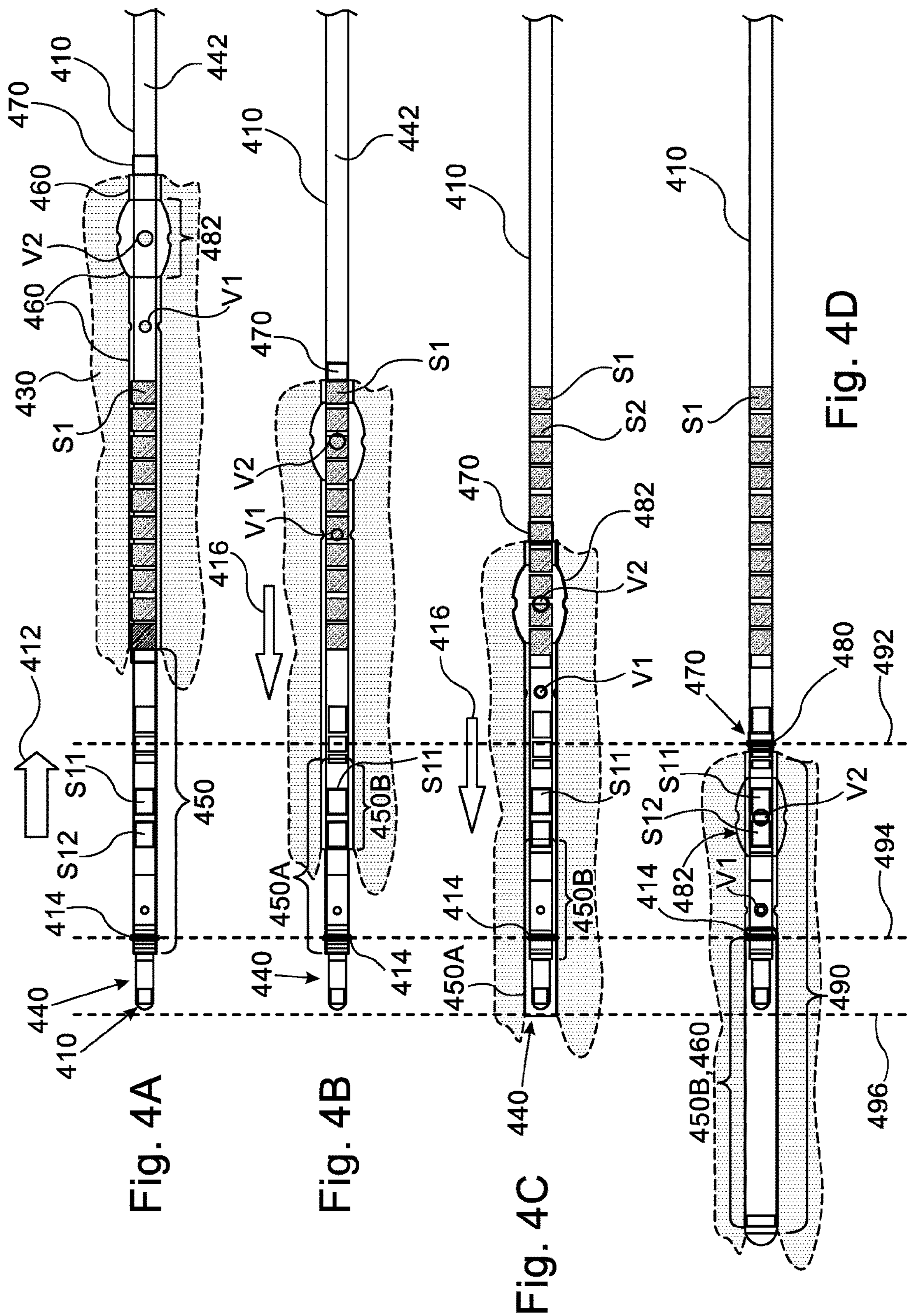
FIGS. 4A-4D illustrate steps of mounting a balloon assembly on anorectal catheter according to an example embodiment of the invention.

The three-section tube may encircle at least a portion of a catheter and it may be concentrically slidable along and over the catheter in a first direction (412). The three-section tube may be slid over the catheter, or over some length thereof, until the proximal end of PCT 450 lines up, or is aligned, with a proximal attachment point on the catheter. Once the proximal end of PCT 450 and a proximal catheter attachment point are aligned, the three-section tube (the proximal end of PCT 450) may be secured/attached in an airtight fashion, at step 320, to proximal end 440 of catheter 410 at a proximal attach point on catheter 410 by using, for example, rubber band or dental floss 414. Catheter 410 may include a vent or through hole or air passage to enable inflation of balloon 430 through an inflation channel/tube inside catheter 410. FIG. 4A illustrates the three-section tube and the balloon mounted on catheter 410, ready for the next assembling steps. The balloon may be inflated through the transfer tube/section. The transfer tube/section may form in conjunction with, or be an extension of, an airway or air path with an inflation channel/tube inside the catheter.

At step 330, with the proximal end of PCT 450 secured in place (414), transfer tube/section 460 is slid in a direction opposite to direction 412; e.g., backwards (in direction 416) on catheter 410 together with DCT 470, towards catheter's proximal end 440, as shown in FIG. 4B. Transfer tube/section 460 and DCT 470 are continued to be slid in direction 416, as shown, for example, in FIG. 4C, until a distal end of DCT 470 lines up, or is aligned, with a distal attach point on the catheter. At step 340, DCT 470 is secured/attached in an airtight fashion to the catheter at the distal catheter attach point by, for example, using a rubber band, string or dental floss 480, as shown in FIG. 4D.

Being flexible and thin, PCT 450 enables sliding transfer, or central, tube/section 460 backwards, in direction 416, over PCT 450 (that is, over itself) while the proximal end of PCT 450 remains secured to the proximal end 440 of the catheter. That is, moving transfer tube/section 460 backwards causes flexible PCT 450 to turn inside out, at least partly, inside transfer tube/section 460. (PCT 450 is at least partly foldable into transfer tube/section 460; i.e., PCT 450 is concentrically folded into transfer tube/section 460 when transfer tube/section 460 is moved backwards.)

Referring again to FIG. 4B and FIG. 4C, PCT 450 is shown having two portions: a first, unfolded, portion 450A, and a second portion 450B that is folded over portion 450A. PCT 450 is shown in FIG. 4A in its initial unfolded state; that is, fully extended. The more transfer tube 460 and DCT 470 are slid in direction 416, the longer the portion 450B of the PCT and, consequently, the shorter the (folded) portion 450A of the PCT. (The overall linear length of PCT 450 is fixed and equal to the sum of the lengths of tube portions 450A and 450B.) While portion 450A shows the external surface of PCT 450, portion 450B shows the inner surface of PCT 450 'pulled outward'. The previously inner surface of PCT 450 becomes—after sliding of transfer tube/section 460 to the left—the external surface thereof. In FIG. 4D, transfer tube/section 460 and DCT 470 are shown slid leftward to a maximum distance that is permitted by the length of PCT 450 (in FIG. 4D, the entire or major length of PCT 450 is shown turned inside out, as shown at 450B), which results in tube/section portion 450B being the longest possible, and PCT 450 being completely or largely contained in transfer tube/section 460. Transfer tube/section 460 may have two vent/through holes, V1 and V2, or air passages to enable inflating of balloon 430 and taking pressure measurements by sensors S11-S12. In FIG. 4D, the whole balloon assembly 490 is shown assembled on catheter 410, ready for use. (Broken lines 492, 494 and 496 are reference lines shown for convenience only.) The rounded tip shown at the proximal end of the catheter/device, for example, in FIG. 4D is optional and it may be added after step 330.

Figure 5A:
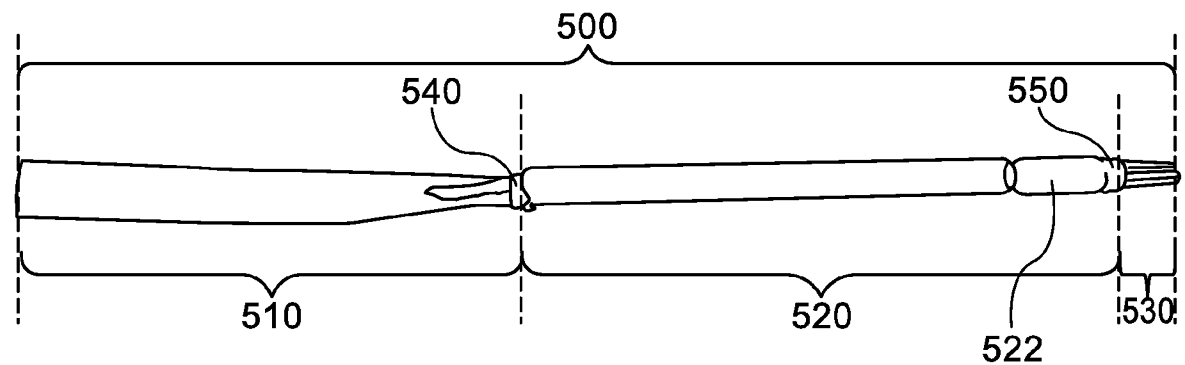
FIG. 5A illustrates a line drawing of a three-part tube according to an example embodiment of the invention.

FIG. 5A depicts a three-section assembly tube 500 according to an example embodiment of the present invention. (FIG. 5A is a line drawing drawn for the picture shown in FIG. 5C.) Assembly tube 500 may include three, functionally distinct, tubes, tubular sections, elements or members: a first tube section 510 (an example PCT) which may be flexible, a second, central, tube section 520 (an example transfer tube) which is referred to herein as transfer tube/section and may be semi-flexible, and a third tube section 530 (an example DCT) which may be flexible. (A tube section may be a separate tube that is lengthwise connected to another tube or tube section. Two, or three, tube sections may be formed in one tube, which may be produced with the respective distinct sections.)

By way of example, PCT 510 may be approximately 120.65 mm long, have an outer diameter of approximately 10 mm and be made of TSP-1051 polyurethane. By way of example, transfer tube 520 may be approximately 152.75 mm long, have an inner diameter of approximately 6.35 mm (¼ inch) and an outer diameter of approximately 7.94 mm (5⁄16 inch), and be made of tygothane C-2010-A polyurethane. By way of example, DCT 530 may be approximately 15 mm long, have a diameter of approximately 6 mm and be made of TSP-1066 2.2 mil polyurethane. (Any of PCT 510, transfer tube 520 and DCT 530 may have material(s) and/or length and/or diameter other than specified herein.)

Tube section (PCT) 510 may be connected or attached to tube section 520 (transfer tube) at its end 540, for example by welding one tube section to the other tube section, or tube section 510 may be an extension of tube section 520. Tube section (DCT) 530 may be connected or attached to tube section 520 at its end 550, for example, by welding it to transfer tube 520, or tube section 530 may be an extension of tube section 520. During mounting of tube 500 on a catheter, tube section 510 is folded inside tube section 520. (Such folding is shown, for example, in FIGS. 4B-4D.) Tube section 520 may include a protective bulge 522 to mechanically protect the catheter's pressure sensors used to measure pressure inside a balloon. A balloon may encircle tube section 520 and be mounted on tube section 520 such that a first end of the balloon may be connected to a first end (e.g., end 540) of tube section 520, and a second end of the balloon (e.g., an end opposite the balloon's first end) may be connected to a second end (e.g., end 550) of tube section 520.

Figure 7:
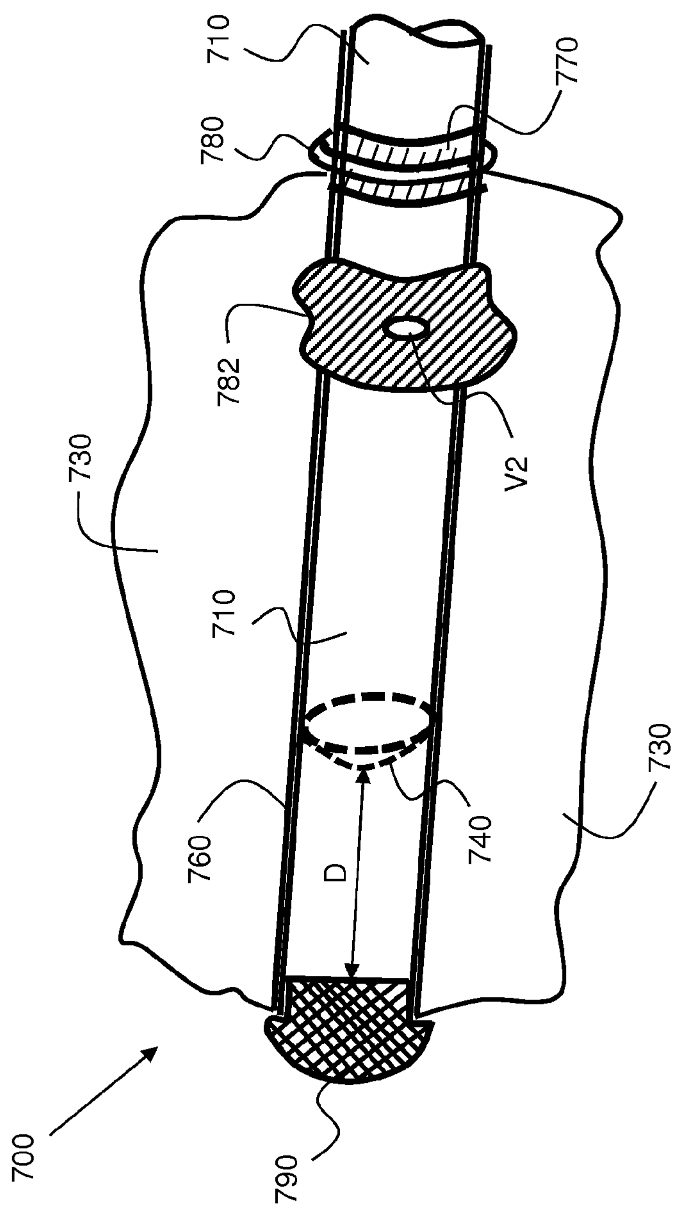
FIG. 7 illustrates a balloon assembly according to another embodiment.

Tube 500 may be configured to encircle at least a portion of a catheter and to concentrically slide along and over the catheter in a first direction (e.g., direction 412, FIG. 4A), and then in a second direction opposite the first direction (e.g., direction 416, FIG. 4B). Tube section 520 is shown lengthwise interposed between tube section 510 and tube section 530. The three tube assembly 500 may be constructed of a single seamless tube, with varying diameter and/or thickness, or two tubes which are seamlessly connected (e.g., as illustrated in FIG. 7), etc.

Figure 5B:
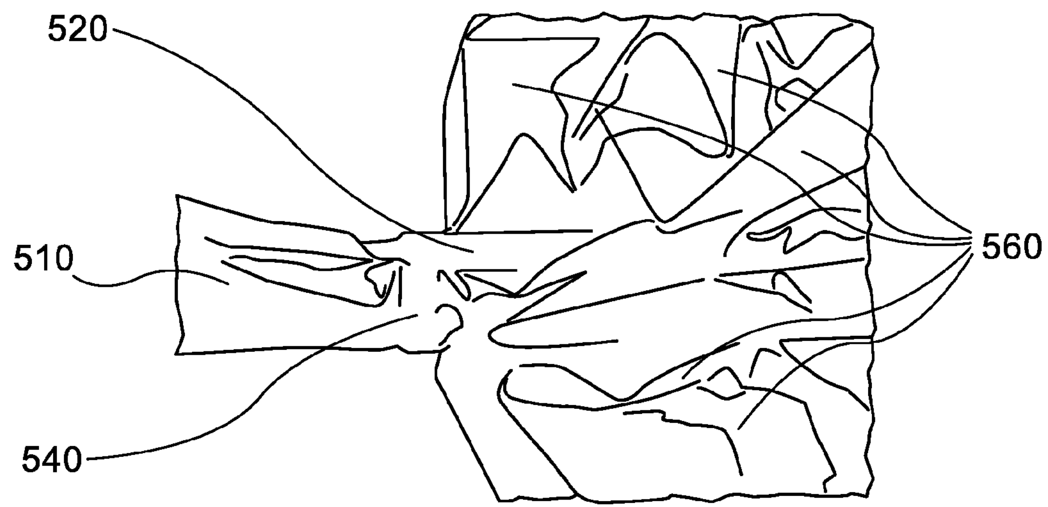
FIG. 5B illustrates a line drawing partly showing a balloon mounted on the three-part tube of FIG. 5A according to an example embodiment of the invention.
Figure 5C:
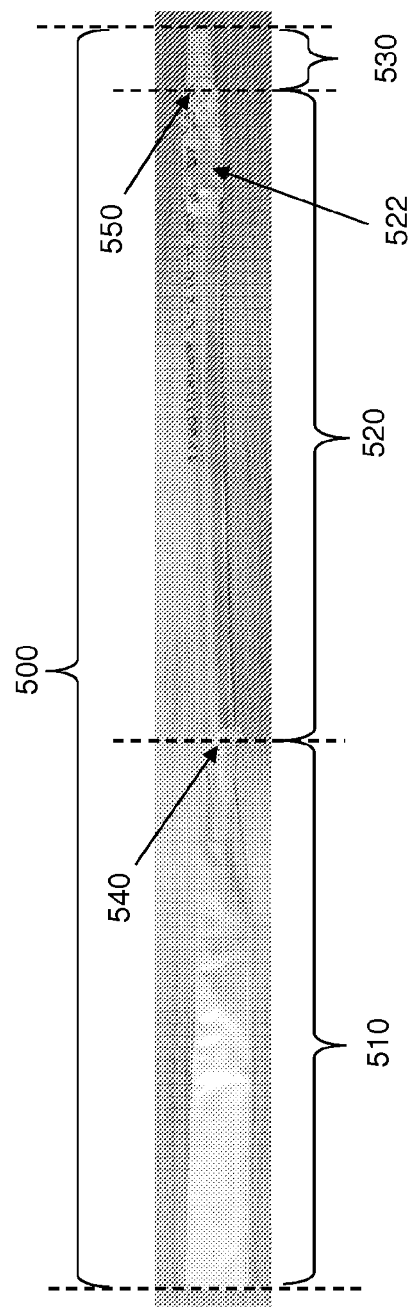
FIGS. 5C and 5D are pictures respectively used as basis for the preparation of the line drawings in FIGS. 5A and 5B.
Figure 5D:
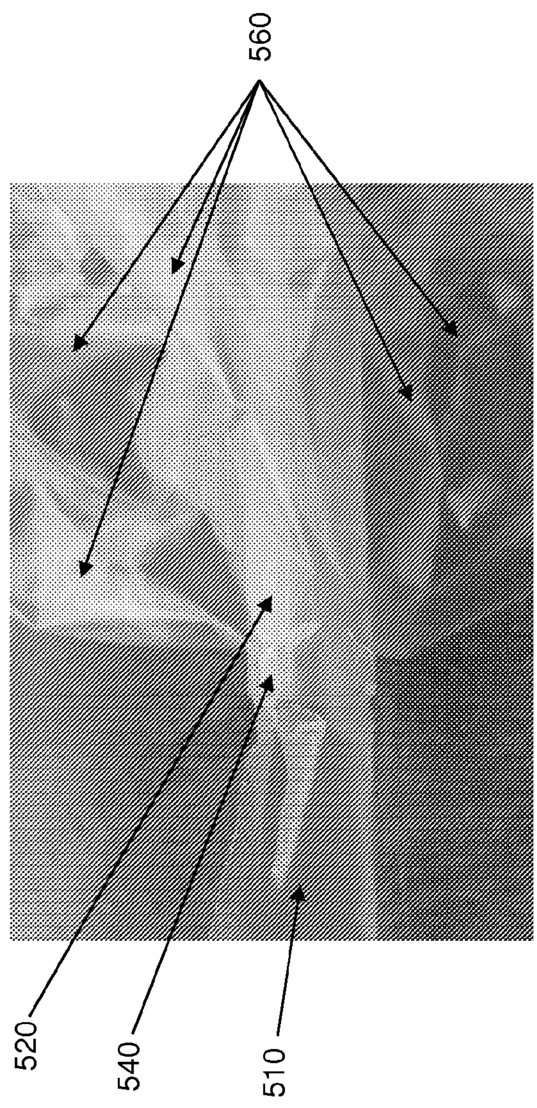

FIG. 5B depicts part of tube 500 of FIG. 5A with part of a balloon 560. (FIG. 5B is a line drawing drawn for the picture shown in FIG. 5D.) Balloon 560, which may be connected or attached (e.g., by welding, gluing or bonding) to proximal end 540 of tube section 520, for example, by welding a first opening or end of balloon 560 to proximal end 540 of tube section 520. A second opening or end of balloon 560 may be connected or attached to a second/opposite end of tube section 520. (The second/opposite opening/end of tube section 520 is not shown in FIG. 5B.) The first and second openings or ends of balloon 560 may respectively be airtight connected (e.g., by welding or bonding) to the ends, or end portions, of tube section 520.

Figure 6A:
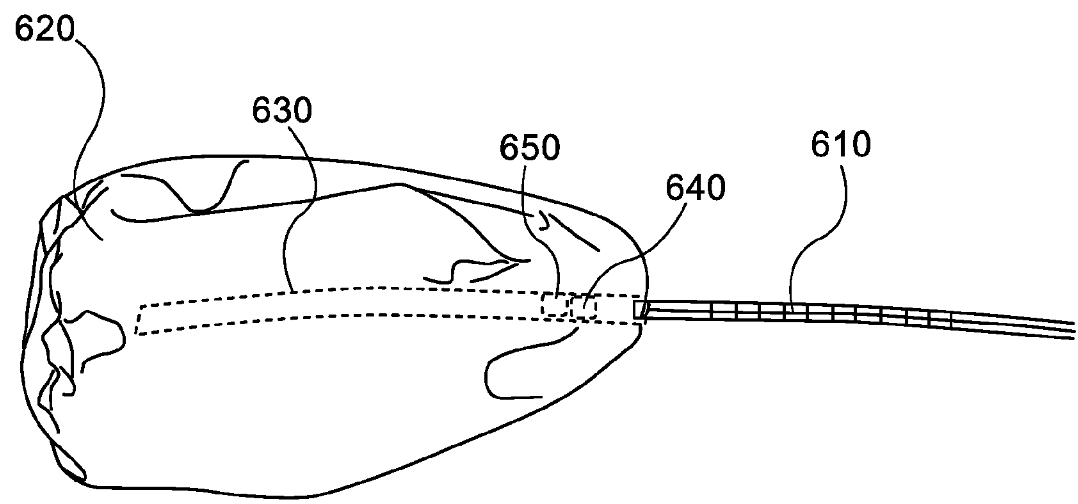
FIGS. 6A-6B illustrate line drawings showing a balloon assembly mounted on a catheter, where the balloon is respectively shown partly inflated (FIG. 6A) and fully inflated (FIG. 6B) according to an example embodiment of the invention.
Figure 6B:
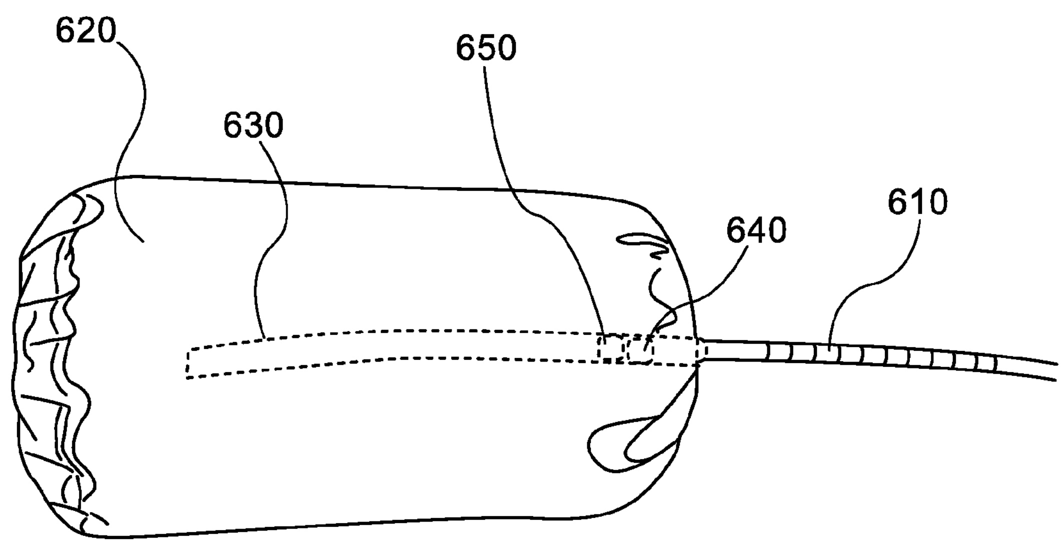
Figure 6C:
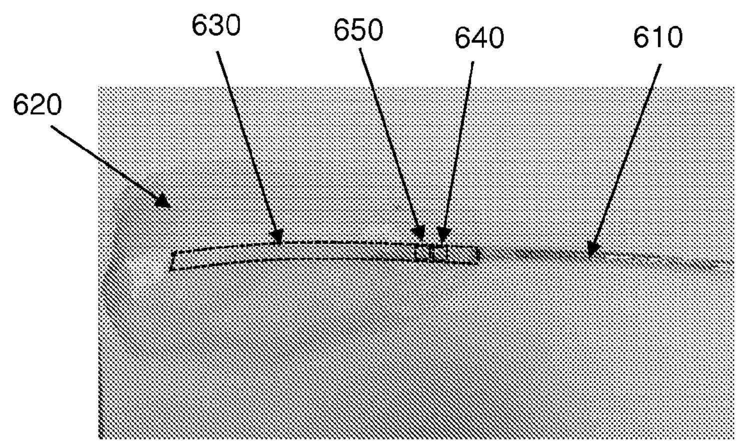
FIGS. 6C and 6D are pictures respectively used as basis for the preparation of the line drawings in FIGS. 6A and 6B.
Figure 6D:
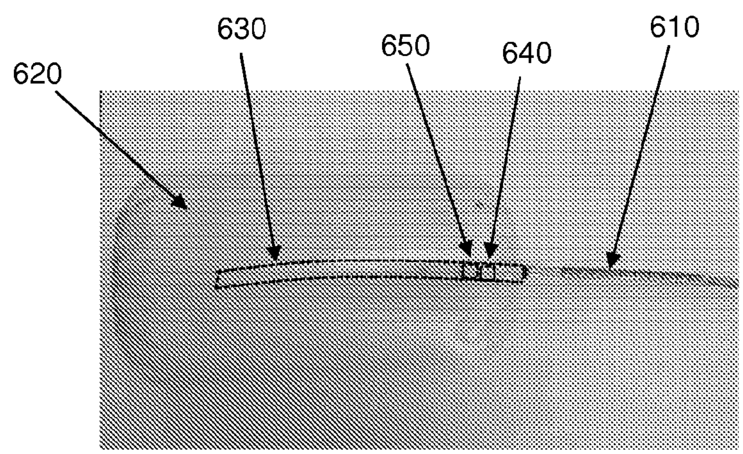

FIGS. 6A-6B depict a catheter 610 with a balloon 620 mounted thereon according to an example embodiment of the present invention. FIGS. 6A-6B show a balloon attached to a catheter only at the distal end of the balloon. (The proximal end of the balloon is free.) However, it is more preferable that both the proximal and distal ends of the balloon be attached to the transfer tube, each end of balloon at a different end of the transfer tube. (FIGS. 6A and 6B are, respectively, line drawings drawn for the pictures shown in FIG. 6C and FIG. 6D.)

In FIG. 6A, balloon 620 is partly inflated. FIG. 6B depicts balloon 620 when fully inflated. The lengthy transfer tube is shown at 630. (The PCT is completely folded inside the transfer tube so it is not shown.) Also shown in FIGS. 6A-6B, inside balloon 620 and highlighted using dotted boxes, are two pressure sensors 640 and 650 which are used to measure pressure inside balloon 620. (Since transfer tube 630 is in balloon 620, it is also highlighted using dotted lines).

FIG. 7 illustrates a balloon assembly 700 according to another embodiment. Balloon assembly 700, which is shown assembled on a catheter 700, may include balloon 730, and a two-section assembly tube that includes only a transfer tube 760 and a DCT 770 (rather than additionally having a PCT). DCT 770 may be attached to/on catheter 710 by using, for example, rubber band or dental floss 780. Transfer tube 760 may include a bulge 782 with one or more vent holes (one vent hole is shown—V2). The distal end or opening of balloon 730 may be attached, in airtight fashion, to DCT 770, or to a distal portion of transfer tube 760.

The proximal end or opening of balloon 730 may be attached, in airtight fashion, to the proximal portion of transfer tube 760. A cap or plug 790 may seal the proximal end or opening of transfer tube 760 in airtight fashion and, at the same time, connect the proximal end/opening of balloon 730 to the proximal end/opening of transfer tube 760 by inserting and pressing the balloon's proximal end/opening inside (onto the inner diameter of) transfer tube 760 by plug 790. Alternatively, cap or plug 790 may be used to seal the proximal end or opening of transfer tube 760 in airtight fashion, and the proximal end/opening of balloon 730 may be connected to the proximal end/opening of transfer tube 760 by pressing the balloon's proximal end/opening outside (onto the outer diameter of) transfer tube 760 by using, for example, a rubber band or a dental floss. Plug or cap 790 may be used to prevent air from escaping out of the proximal end of transfer tube 760. Transfer tube 760 may be closed/sealed at its proximal end by any air tight means, and the proximal end of balloon 730 may be fastened to transfer tube 760 at the transfer tube's outer diameter in this area. (Plug or cap 790 may function like, and thus replace, the PCT in preventing air from escaping the balloon assembly.)

The distance (D) between proximal end 740 of catheter 710 and plug/cap 790 may be relatively small or large. A desired operational distance D may be set by sliding the whole balloon assembly (e.g., transfer tube 760, DCT 770, balloon 730) to the left hand side and securing the assembly to catheter 710 by, for example, rubber band 780, or by selecting a transfer tube with a suitable length, assuming that the distal connection point, line or area on catheter 710 is fixed or unchangeable. (The catheter's sensors, and other elements thereof, are not shown in FIG. 7.)

Each of transfer tube/section 760 and distal connection tube 770 may be made of or include any of the materials specified herein, or other materials or additional materials, and any such tube/section may have any operational length and diameter and thickness specified herein, or other operational length and/or diameter and/or thickness.

The articles "a"/"an" are used herein to refer to at least one) of the grammatical object of the article, depending on the context. For example, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. Having described exemplary embodiments of the invention, it will be apparent to those skilled in the art that modifications of the disclosed embodiments will be within the scope of the invention. Alternative embodiments may, accordingly, include more elements (e.g., sealing elements or material) or functionally equivalent elements. The present disclosure is relevant to various types of catheters that use a balloon to measure pressure or other parameter. Hence the scope of the claims that follow is not limited by the disclosure herein.

The invention claimed is:

1. A balloon assembly for an anorectal manometry catheter, the balloon assembly comprising:

a tube to encircle a portion of a catheter, the tube comprising:

a distal connection tube having a first end and a second end;

a proximal connection tube having a first end and a second end;

a transfer tube having a first end and a second end and lengthwise interposed between, and connected to, the distal connection tube and proximal connection tube such that the second end of the distal connection tube is connected to the first end of the transfer tube and the first end of the proximal connection tube is connected to the second end of the transfer tube, such that the transfer tube is slidable over the catheter while the proximal end of the proximal connection tube remains secured to the catheter; and a balloon having a first opening connected to the first end of the transfer tube and a second opening connected to the second end of the transfer tube, wherein the distal connection tube, the proximal connection tube, and the transfer tube form a tube with varying diameter and/or thickness.

2. The balloon assembly as in claim 1, wherein the proximal connection tube is at least partly foldable into the transfer tube.

3. The balloon assembly as in claim 1, wherein the balloon is inflatable through the transfer tube.

4. The balloon assembly as in claim 3, wherein the transfer tube comprises a hole or air passage to enable inflation of the balloon.

5. The balloon assembly as in claim 1, wherein the transfer tube includes a bulge.

6. The balloon assembly as in claim 5, wherein the bulge comprises a hole to enable measurement of pressure inside the balloon by pressure sensors included in the catheter.

7. The balloon assembly as in claim 5, wherein the bulge comprises a hole to enable inflation of the balloon.

8. The balloon assembly as in claim 1, wherein the diameter of the distal connection tube, transfer tube and proximal connection tube are within the range 4 mm-10 mm.

9. The balloon assembly as in claim 1, wherein the thickness of the proximal connection tube, transfer tube and distal connection tube are respectively within the 0.01 mm-0.5 mm, 0.1 mm-4.0 mm and 0.01 mm-0.5 mm ranges.

10. The balloon assembly as in claim 1, wherein the proximal connection tube comprises polyurethane, distal connection tube comprises thermoplastic elastomer, and the transfer tube comprises polyurethane.

11. The balloon assembly as in claim 1, wherein the proximal connection tube comprises TSP-1051 polyurethane, the distal connection tube comprises XFlex Styrene-Ethylene-Butylene-Styrene (SEBS), and the transfer tube comprises C-210-A polyurethane.

* * * * *